United States Patent [19]
Flaherty

[11] Patent Number: 4,755,382
[45] Date of Patent: Jul. 5, 1988

[54] IMMUNOSTIMULATING METHOD

[75] Inventor: Dennis K. Flaherty, Ballwin, Mo.

[73] Assignee: Monsanto Company, St. Louis, Mo.

[21] Appl. No.: 744,447

[22] Filed: Jun. 13, 1985

[51] Int. Cl.[4] .............................................. A61K 39/02
[52] U.S. Cl. ....................................... 424/92; 424/88; 424/85; 424/87; 514/885
[58] Field of Search ........................ 424/88, 92, 85, 87; 514/885

[56] References Cited

U.S. PATENT DOCUMENTS 4,057,685 11/1977 McIntire ................................ 424/92
4,455,142 6/1984 Martins et al. ....................... 604/890
4,484,923 11/1984 Amkraut et al. .................... 604/897

OTHER PUBLICATIONS

Usinger et al., *Fed Proc* 44(3) 1985 p. 598.
Usinger et al., Fed Proc 43(6) 1984 p. 1492.
Flaherty et al., *Inf and Imm* vol. 43(1) 1984 pp. 213–216.
Usinger et al., Curr Microbiol 12(4) 1985 (Abst.).
Usinger et al., Abstr Annu Mut Am Soc Microbiol 85 (0) 1985.
Usinger et al., Fed Proc 42(3) 1983 (Abst).

*Primary Examiner*—John Kight
*Assistant Examiner*—Garnette Draper
*Attorney, Agent, or Firm*—Scott J. Meyer; James W. Williams, Jr.

[57] ABSTRACT

A method is disclosed for stimulating the immune system of a warm-blooded animal by the production of antibodies by administering an effective amount of *Cytophaga allerginae* lipopolysaccharide endotoxin.

2 Claims, 1 Drawing Sheet

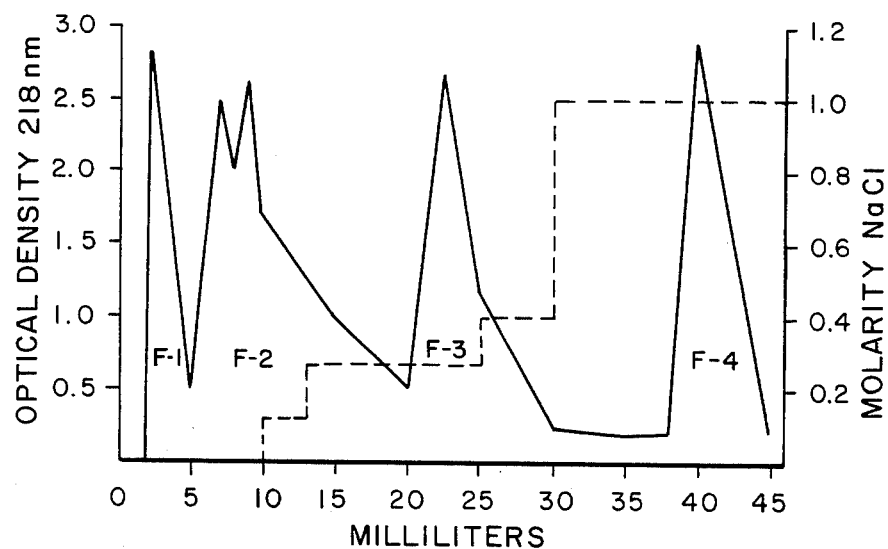

IMMUNOSTIMULATING METHOD

BACKGROUND OF THE INVENTION

This invention relates to a method of stimulating the immune system of a warm-blooded animal by the production of antibodies.

It is well-known that warm-blooded animals have several types of cells which constitute various lines of defense of the body against the invasion of foreign agents. One line of defense involves the leukocytes and macrophages in the blood stream which are capable of phagocytizing the foreign agent and often destroying it when such cells come in contact with the foreign agent.

Another line of defense involves an immune mechanism which is brought into action by the antigenic constituent of the foreign agent. One type of immune mechanism involves the B-cells which are precursors of cells that secrete immunoglobulins (Igs) or antibodies. The immunoglobulins or antibodies play a significant role in the fight against infection caused by bacteria or other infectious microorganisms.

Consequently, methods of stimulating the immune system to produce antibodies are useful for immune-deficient patients.

It is known that different B-cell mitogens stimulate secretion of distinctive patterns of immunoglobulin classes and subclasses in murine systems. For example, lipopolysaccharides (LPS) stimulate IgM, IgA, IgG3 and IgG2b; *Corynebacterium parvum* stimulates IgM, IgA, IgG1 and IgG3; and pokeweed mitogen stimulates IgM, IgA, IgG1, IgG2a, IgG2b and IgG3.

Bacterial endotoxins are complex molecules that contain lipopolysaccharides. Although these endotoxins can stimulate antibody production, they exhibit extreme toxicity which appears to reside in their lipid fraction. When injected in sufficient amounts, they usually cause irreversible shock within an hour our two.

BRIEF DESCRIPTION OF THE INVENTION

The present invention relates to a method of stimulating the immune system of a warm-blooded animal by the production of antibodies which comprises administering to said warm-blooded animal an effective amount of *Cytophaga allerginae* endotoxin. The use of this method is enhanced by the relative non-toxicity of the endotoxin in comparison to conventional endotoxins such as from Salmonella which are known to be highly toxic.

BRIEF DESCRIPTION OF THE DRAWING

FIG. 1 shows the chromatographic profile of the phenol extract of *Cytophaga allerginae* from anion exchange chromatography.

DETAILED DESCRIPTION OF THE INVENTION

Cytophaga is a genus of bacteria classified in Bergey's Manual of *Determinative Bacteria,* Buchanan and Gibbons, Eds., 8th ed., 1977, Williams and Wilkins Co., Baltimore, pp. 101-104. Members of the genus are common in soil and in both freshwater and marine environments. Species of the Cytophaga have not generally been shown to initiate human disease, although the endotoxin of *Cytophaga allerginae* has been described as a putative agent of occupation related lung disease. See Flaherty et al., *Infect. Immun.* 43(1), 206–216 (1984).

The isolation and characterization of the *Cytophaga allerginae* species are disclosed by Liebert et al., *App. Environ. Microbiol.* 39, 936–943 (1984). An isolate of the organism was obtained from a biomass growing in the demister vanes in a chilled (16° C.) water spray air humidification system. This chilled-water spray humidification system was installed in a textile-producing facility to provide humidity and temperature control. To humidfy air by this system, ambient outside air was filtered and drawn through a chilled-water (16° C.) spray. After humidification, large water droplets were removed by passage through aluminum demister vanes set at angles to the direction of air flow.

An isolate of this species which contains a biologically active endotoxin, designated WF-164, was made available to the public by being deposited without restriction in the permanent collection of the American Type Culture Collection, Rockville, Md., under accession number ATCC 35,408. Samples of this strain can be obtained by the public upon request to that depository.

The morphology and culture characteristics of *Cytophaga allerginae* as disclosed by Liebert et al., Ibid., are as follows:

The organism was determined to be a gram-negative, elongated, flexious bacillus. Transmission election microscopy (TEM) negative staining of whole mounts with 2.0% ammonium molybdate revealed nonflagellated cells measuring 0.3 by 3.5 to 9.0 $\mu$m. After 24 h of growth at room temperature (ca. 23° C.) on nutrient agar (NA), the cells had an average length of 3.5 $\mu$m; in nutrient broth (NB), the average cell length measured 4.4 $\mu$m, although longer cells were observed after being grown in 1% peptone water. The average cell length was 8.9 $\mu$m after 24 h of growth.

The ultrastructure of the organism revealed a bacillus having a gram-negative cell envelope with a trilaminar inner membrane (cytoplasmic membrane), an intermediate layer (peptidoglycan), and a convoluted, trilaminar outer membrane (lipopolysaccharide). There was found an increased density of the cell wall in TEM preparations treated with ruthenium red. Vesicular tubular structures similar to those observed on the surfaces of *Cytophaga johnsonae* C4 and Flexibacter sp. strain BH3 were observed on the surfaces of the *Cytophaga allerginae.*

Gliding and flexing movements were observed by light microscopy on solid surfaces and in liquid cultures. Typical spreading, fingerlike projections of the bacterial colonies were observed on both Cytophaga and vy/2 agars. No fruiting bodies or microcysts were observed. In older cultures, autolysis and spheroplasts were observed. The organism produced a bright yellow pigment when grown on all culture media. The extracted pigment demonstrated a maximum absorption peak at 450 nm. suggesting either a carotenoid or a flexirubin-type pigment. The KOH-flexirubin test was positive.

The *Cytophaga allerginae,* originally isolated on plate count (PC) agar at 20° C., also grew at 10 or 30° C. but not at 4 or 37° C. Growth was observed within the pH range from 5.5 to 9.5 and in NB with 1.5% NaCl but not with 3.0% NaCl. Growth occurred on eosin methylene blue (EMB) agar but not on MacConkey agar. Anaerobic growth was observed in half-strength NB and on PC agar after 48 h. However, noticeably more luxuriant growth occurred on the same media incubated aerobically.

Of the macromolecules examined, chitin, starch, carboxymethyl cellulose, caesin, and gelatin were hydrolyzed, whereas cellulose, agar, and alginate were not hydrolyzed. Results of the other biochemical tests are given in Table 1, below. Of the 11 antibiotics tested, chloramphenicol, carbenicillin and tetracycline were inhibitory to *Cytophaga allerginae.*

Comparison of the cellular fatty acid content of *Cytophaga allerginae* with those of several reference strains revealed a lipid profile similar to those of *C. Aquatilis, C. johnsonae,* and also *Flexibacter aurantiacus.* Little difference in the relative concentrations of straight- and branch-chain fatty acids of *Cytophaga allerginae* and the three reference strains was detected. Methyltetradecenoic acid was the major lipid (45% of the total fatty acids) detected in all four of these strains. However, there were differences in the relative concentrations of straight- and branched-chain fatty acids of *Cytophaga allerginae* and the species of Flavobacterium.

Whole-cell carbohydrate composition demonstrated little similarity between *Cytophaga allerginae* and any of the Flavobacterium reference strains. *Cytophaga allerginae* contained a higher percentage of N-acetyl-D-galactosamine (20.9%) than the reference Cytophaga spp. and Flavobacterium spp. Also, unlike the other reference strains analyzed, the highest percentage of total carbohydrates of *Cytophaga allerginae* was composed of two components, heptose and dideoxyhexosamine, which eluted at the same retention time on packed columns.

Finally, *Cytophaga allerginae* was determined to have a DNA base composition of 34.8 mol% of G+C (mean of five determinations). DNA homology studies demonstrated a 77.8% similarity of *Cytophaga allerginae* to *C. aquatilis.*

TABLE 1

| Biochemical Characteristics of *Cytophaga allerginae* | |
|---|---|
| Characteristics | Result[a] |
| Polysaccharide degradation | |
| Cellulose | − |
| Carboxymethyl cellulose | + |
| Chitin | + |
| Agar | − |
| Alginate | − |
| Casein | + |
| Starch | + |
| Gelatin | + |
| Carbohydrate utilization[b] | |
| Glucose oxidation | + |
| Lactose oxidation | − |
| Maltose oxidation | + |
| Cellobiose oxidation | + |
| Sucrose oxidation | − |
| Arabinose oxidation | + |
| Glucose fermentation | − |
| Other | |
| Cytochrome oxidase production | + |
| Catalase production | + |
| β-Galactosidase production | + |
| Phenylalanine deaminase | − |
| Arginine dihydrolase | − |
| Lysine decarboxylase | − |
| Ornithine decarboxylase | − |
| Urease production | − |
| DNase production | − |
| Hydrogen sulfide production | − |
| Lecithinase production | − |
| Acetylmethycarbinol production | − |
| Methyl red test | − |
| Indole production | − |
| Nitrate reduction | − |
| Antibiotic susceptibility (amt)[c] | |
| Ampicillin (10 μg) | − |

TABLE 1-continued

| Biochemical Characteristics of *Cytophaga allerginae* | |
|---|---|
| Characteristics | Result[a] |
| Bacitracin (10 U) | − |
| Carbenicillin (50 μg) | + |
| Cephalothin (30 μg) | − |
| Chloramphenicol (30 μg) | + |
| Gentamicin (10 μg) | − |
| Neomycin (30 μg) | − |
| Penicillin (10 U) | − |
| Polymyxin B (300 U) | − |
| Streptomycin (10 μg) | − |
| Tetracycline (30 μg) | + |

[a] +, Positive result: −, negative result
[b] Production of acid in Board and Holding medium, J. Appl. Bacteriol. 23. XI-XII(1960).
[c] +, inhibitory: −, not inhibitory to *Cytophaga allerginae.*

Isolation and purification of the lipopolysaccharide endotoxin from *Cytophaga allerginae* can be carried out by methods described by Flaherty et al., *Infect. Immun.* 43(1), 206–213 (1984), the disclosure of which is incorporated herein by reference. According to these methods, the lipopolysaccharide endotoxin preferably is obtained by a phenol-water extraction of a culture of the organism followed by purification by anion exchange column chromatography of the extracts.

In a preferred method, the endotoxin was extracted and purified as follows:

Phenol-Water Extract

*Cytophaga allerginae,* WF.-164, was grown in nutrient broth (Difco, Detroit, Mich.) at 23° C. for 14 days. The bacteria were recovered from the broth by centrifugation and washed twice with 0.85% saline. The lipopolysaccharide (LPS) fraction was then recovered by using a 5-min phenol-water extraction as described by Westphal and Jann, *Methods Carbohydr. Chem.* 5, 83–92 (1965). The water layer was recovered and dialyzed against deionized water for 24 to 48 h at room temperature, using 30 changes of water. After dialysis, the concentration of phenol in the dialysate was determined by UV adsorption at 278 and 283 nm, using a phenol-water calibration curve. The dialysates contained $\leq 2.0$ ppm ($\leq 2.0$ μg/ml) of phenol. By high-pressure filtration, the LPS fractions were filtered through a 0.45 μm filter (Millipore). The eluate was then concentrated 10-fold by high-pressure filtration, using Spectra stirred cells with 10,000-molecular weight cutoff filters. The retained LPS fractions with molecular weights of >10,000 were lyophilized.

Anion Exchange Purification

The LPS recovered by the phenol extraction was fractionated by anion-exchange chromatography using a DEAE-Sepharose CL-6B (Pharmacia Fine Chemicals, Inc., Piscataway, N.J.) column (10 by 1.5 cm). All extracts were equilibrated with the starting buffer, 0.05M potassium phosphate buffer (pH 7.2) with 0.15M NaCl, and eluted with a stepwise salt gradient (0.15 to 1.0M NaCl in the phosphate buffer).

The chromatographic profile of the phenol extract of the *Cytophaga allerginae* while subjected to the aforesaid anion exchange purification is shown in the accompanying FIG. 1. The solid line denotes absorbance (optical density) at 218 nm; the broken line shows salt gradient. Endotoxin activity resided principally in fraction 1. Conversely, fraction 4 contained one-tenth the endotoxin activity of fraction 1. When compared with an *E.* coli standard curve, fraction 1 (F-1) had a computed endotoxin equivalent of 1.21 ng/ml at a dilution of 7.8 ng/ml or 15.5% (wt/wt).

The chemical constituents present in the above column purified fraction (F-1) are shown in Table 2, below.

TABLE 2
Chemical Constituents of *Cytophaga allerginae* endotoxin

| Constituent | % |
|---|---|
| Carbohydrate[a] | |
| Glyceraldehyde | 0.2 |
| Rhamnose | 2.8 |
| Fucose | 1.1 |
| Ribose | 0.1 |
| 2-Deoxyribose | 0.2 |
| Arabinose | 0.1 |
| Mannose | 1.4 |
| Galactose | 0.6 |
| Xylose | 0.1 |
| Glucose | 1.9 |
| Heptose | 33.9 |
| N—Acetylgalactosamine | 5.1 |
| N—Acetylglucosamine | 18.1 |
| Phosphorus | 0.57 |
| RNA | ≦0.15 |
| Water | 20.0 |
| Lipid[b] | |
| 11:0 | —[c] |
| 12:0 | Tr[d] |
| 13:0 | — |
| 13:1 | — |
| 14:0 | 5.0 |
| 2OH 14:0 | Tr |
| 3OH 14:0 | Tr |
| 14:1 | 2.0 |
| 15:0 | 9.0 |
| i15:0 | 7.0 |
| a15:0 | 16.0 |
| 15:1 | — |
| 16:0 | 23.0 |
| 16:1 | 17.0 |
| 17:0 | — |
| i17:0 | 3.0 |
| a17:0 | Tr |
| 17:1 | Tr |
| 18:0 | 3.0 |
| 18:1 | 11.0 |
| 19:0 | — |
| 19:1 | — |
| 20:0 | — |

[a]Results expressed as percentage (weight/weight) of total.
[b]Results expressed as percentage of total lipid.
[c]—, Not detected.
[d]Tr = ≦2% of total lipid.

The manner of administering the *Cytophaga allerginae* endotoxin to a warm-blooded mammal can be, for example, by intraperitoneal, subcutaneous, intradermal or intramuscular administration. The endotoxin is thus administered in a pharamceutically acceptable carrier, for example, sterile water or physiological saline, preferably in amounts of from about 0.001 to about 1 mg/kg of body weight. Pharmaceutically acceptable carriers and their methods of compounding are well-known and can be selected by reference to a common text such as *Remington's Pharmaceutical Sciences,* Mack Publishing Co., Easton, Pa., 11th edition, 1980.

$LD_{50}$ Determinations

The $LD_{50}$ of *Cytophaga allerginae* lipopolysaccharide endotoxin isolated by the above phenol extraction method and purified by the foregoing anion-exchange chromatography method was determined as follows:

The animals used in this determination were male Crl: CD-1 (ICR) BR albino mice obtained at 28 days of age from Charles River Breeding Laboratory, Portage, Mich. The mice were subjected to routine quarantine procedures for 10 days and were released in good condition. The mice were double-housed until put on test at which time they were single-housed in stainless steel, suspended cages. They were provided food (Ralston Purina Certified Rodent Chow #5002) and water ad libitum.

The two test materials were identified as *Salmonella typhosa* 0901, Control #688706, lot #3124-25 and *Cytophaga allerginae,* B.I. 164 (no lot #) endotoxins. The various dosages were prepared by diluting concentrated solutions with physiological saline (0.9% Sodium Chloride Injection USP, American Hospital Supply Corp., Irvine, CA 97714, lot #B4L874C). Injections were done intraperitoneally using a syringe with a 23 ga×1" needle. Each mouse was given a single dose injection with volumes ranging from 0.2 to 0.6 ml, and was observed at least twice daily for two weeks. Dead mice were removed and discarded without necropsy.

Initial dosages were based on previous experience (Cytophaga—100 μg/mouse killed 2 of 4) or literature (*Salmonella typhosa*—range of $10^3$ to $10^6$ μg/kg was an approximate $LD_{50}$). At each of the following dosages (mg/kg) five mice were innoculated:

| Cytophaga | Salmonella |
|---|---|
| 40 | $10^3$ |
| 20 | $10^6$ |
| 10 | $6.7 \times 10^7$ |
| 5 | $3.3 \times 10^7$ |
| 2.5 | $10^9$ |
| 1.25 | |

Early indications were that the mice injected with Salmonella endotoxin were not ill, so another set of five mice per level were injected with fresh solutions. This time, however, 50 mgs of lypholized material was weighed out rather than 1 mg. This necessitated two additional dilutions and one mouse was injected with a quantity of each of these "stock" solutions (1 at 50 mg/kg and 1 at 1 mg/kg). The former mice died while none of the mice at 1 mg/kg or lower died. Also, an insufficient number of the mice injected with the Cytophaga endotoxin died to permit a satisfactory estimate of the dose-response. Therefore, the final series of dose levels (mg/kg) were escalationed to ascertain the dose-response curve:

| Cytophaga | Salmonella |
|---|---|
| 240 | 100 |
| 160 | 50 |
| 80 | 20 |
| | 5 |

The results were as follows:

| *Cytophaga allerginae* | | *Salmonella typhosa* | |
|---|---|---|---|
| Dose | # dead/# injected | Dose | # dead/# injected |
| 240 | 5/5 | 100 | 5/5 |
| 160 | 5/5 | 50 | 5/5 |
| 80 | 4/5 | 20 | 4/5 |
| 40 | 2/5 | 5 | 5/5 |
| 20 | 0/5 | 1 | 0/1 |
| 10 | 1/5 | $10^3$ | 0/10 |
| 5 | 0/5 | $10^6$ | 0/10 |
| 2.5 | 0/5 | $6.7 \times 10^7$ | 0/10 |

-continued

| Cytophaga allerginae | | Salmonella typhosa | |
|---|---|---|---|
| Dose | # dead/# injected | Dose | # dead/# injected |
| 1.25 | 0/5 | $3.3 \times 10^7$ | 0/10 |
|  |  | $10^9$ | 0/10 |

Computer calculated probit responses based on the above results (superfluous dose levels with zero responses were not entered) were as follows:

| Cytophaga allerginae | | | Salmonella typhosa* |
|---|---|---|---|
| LD Value | Results (mg/kg) | 95% C.I. | Results (mg/kg) 95% C.I. |
| 90 | 116.20 | 67.188–462.14 | 1.921 |
| 50 | 40.735 | 22.535–71.638 |  |
| 10 | 14.280 | 3.352–25.039 |  |

*The only obtainable estimate based on the responses (Salmonella) was from nonlinear interpolation using the binominal method.

The foregoing $LD_{50}$ determinations show that the *Cytophaga allerginae* lipopolysaccharide endotoxin has an $LD_{50}$ of about 40 compared to the $LD_{50}$ of about 2 for the *Salmonella typhosa* endotoxin.

Immunostimulant Activity

The induction of de novo human immunoglobulin synthesis—IgG, IgA and IgE—by *Cytophaga allerginae* lipopolysaccharide endotoxin (CAE) isolated and purified by the foregoing method was determined by the standard pokeweed mitogen stimulated immunoglobulin synthesis method. This standard method is described, for example, by Saxon, *Manual of Clinical Immunology*, Eds. Rose and Friedman, ASM, Washington, D.C., Second Edition, 1980, pp. 151–156; and Sampson and Buckley, *J. Immunol.* 127, 829–834 (1981). According to this method, the effect of pokeweed mitogen on human peripheral blood lymphocytes cultured in complete media is determined. The stimulating effect of the CAE is then assessed by adding varying concentrations of the CAE to the media instead of the pokeweed mitogen and comparing the respective results.

In order to determine whether CAE can induce immunoglobulin synthesis by human peripheral blood lymphocytes (PBL) in vitro, human PBL were purified and cultured with either pokeweed mitogen (PWM) at 2.5 and 5 μg/ml, or CAE (1.25–20 μg/ml) for six to ten days. Following that incubation, the supernatants were harvested and the levels of the different immunoglobulins (IgG, IgA and IgE) were determined by either the alkaline phosphatase ELISA assay (IgG and IgA) or the Avidin-Biotin ELISA assay (IgE).

ELISA (enzyme linked immunosorbent assay) is a conventional serology assay technique originally introduced by Engvall and Perlman, *Immunochem.* 8, 871–874 (1971) and *J. Immunol.*. 109, 129–135 (1972). It uses enzyme markers conjugated to antigen or antibody instead of radioactive isotopes or fluorescent dyes and is well adapted to the quantitative assay of immunoglobulins, e.g. IgG. The enzymatic activity is detectable with conventional photometric instrumentation. That is, the antigen or antibody complex can be detected by the enzyme label changing the color of an added substrate. The optical density of the final color is directly proportional to the amount of the unknown antibody or antigen in the original test solution. In the alkaline phosphatase method, that enzyme is comjugated to the antigen (e.g., IgG) such as by the use of glutaraldehyde, and the added substrate is p-nitrophenyl phosphate which is hydrolyzed to p-nitrophenol having a yellow color that can be measured at 405 nm. Further background information on this assay can be had by reference to Voller, Bidwell and Bartlett, "The Enzyme Linked Immunosorbent Assay (ELISA)," Dynatech Laboratories, Inc., Alexandria, Va.

The ELISA determinations were carried out as follows:

Immulon II plates were coated with optimal concentrations of affinity purified antisera to human immunoglobulins (IgG, IgA and IgE). After incubation overnight at 4° C., the plates were washed with phosphate buffered saline (PBS). Unbound reactive sites were blocked with 1% bovine serum albumin in PBS. Following incubation at room temperature for one hour, plates were washed with PBS. Standard concentrations of immunoglobulins, controls and test samples were added to the plates, incubated for two hours at 37° C. and washed with PBS. Two secondary amplification methods were used to detect and quantitate immunoglobulin classes or isotypes.

(1) Alkaline Phosphatase ELISA: Optimal concentrations of anti-human immunoglobulin isotype linked to alkaline phosphatase was added to the plates. The plates were incubated at 37° C. for two hours and washed with PBS. Dinitrophenyl phosphate substrate was added and the plates incubated in the dark for 30 minutes at room temperature. The reaction was terminated with NaOH. The absorbance at 405 nm was determined for each well.

(2) Biotin-Avidin ELISA: Optimal concentrations of biotin conjugated anti-human immunoglobulin isotype were placed in the plate. Following incubation for two hours at 37° C., the plates were washed with PBS. Optimal concentrations of Avidin D horse radish peroxidase (Vector Laboratories, San Francisco, Calif.) were added to the plates, incubated for 30 minutes at 37° C. and washed with PBS. O-phenylene diamine substrate (Zymed Labs, San Francisco, Calif.) was added to the plates. The plates were incubated for 30 minutes at room temperature in the dark. The absorbance was determined at 492 nm.

The assay results set forth in Tables 3 to 5, below, indicate that CAE added to cultures in vitro induces IgG, IgA and IgE synthesis by human PBL. In these tables, the IgG and IgA is reported as nanograms/ml of antibody produced while IgE is reported as picograms/ml of antibody produced. It is seen that CAE induces IgG and IgA synthesis comparable to or greater than the synthesis induced by the commonly used PWM mitogen. CAE also induces de novo IgE synthesis in seven out of ten donors while PWM induces de novo IgE synthesis in four out of ten donors. In summary, CAE is a useful immunostimulant which can induce human IgG, IgA and IgE synthesis in vitro (see Tables 3, 4 and 5). In addition, CAE cultured with human PBL for 6 days induces fibroblast like cells which differ from the morphology of PBL incubated with PWM for six days.

TABLE 3

De novo IgG synthesis ng/ml

| µg/ml Mitogen | | Donor # 1 | 2 | 3 | 4 | 5 | 6 | 7 | 8 | 9 | 10 |
|---|---|---|---|---|---|---|---|---|---|---|---|
| PWM | 5 | 1,940 | 380 | 420 | 960 | 140 | >20,000 | 680 | >20,000 | >20,000 | >20,000 |
|  | 2.5 | 2,540 | 340 | 640 | 280 | 200 | >20,000 | 1160 | >20,000 | >20,000 | >20,000 |
| CAE | 20 | 280 | 240 | 380 | 180 | 3060 | 5,400 | 2500 | 16,760 | 12,880 | >20,000 |
|  | 10 | 0 | 60 | 640 | 340 | 1860 | 2,000 | 840 | 16,160 | 3,680 | >20,000 |
|  | 5 | 0 | 80 | 620 | 240 | 3460 | 720 | 340 | >20,000 | 3,080 | >20,000 |
|  | 2.5 | 0 | 60 | 140 | 120 | 2160 | 700 | 1440 | 15,200 | 1,560 | >20,000 |
|  | 0.25 | 0 | 100 | 420 | 0 | 1660 | 600 | 680 | 18,160 | 1,040 | 15,000 |
| None |  | 20 | 134 | 200 | 140 | 2060 | 0 | 350 | 4,960 | 150 | 5,900 |
| Freeze Thaw 5× |  | 260 | 160 | 520 | 400 | 540 | 0 | 400 | 240 | 320 | 200 |

TABLE 4

IgA Synthesis ng/ml

| ug/ml Mitogen | | Donor # 1 | 2 | 3 | 4 | 5 | 6 | 7 | 8 | 9 | 10 |
|---|---|---|---|---|---|---|---|---|---|---|---|
| PWM | 5 | 39.5 | 32 | 40 | 23 | 42.2 | >1000 | 48.6 | 660 | 935 | 482 |
|  | 2.5 | 23.5 | 34 | 44 | 19 | 35.6 | 640 | 90.6 | 260 | 775 | 242 |
| CAE | 20 | 1.5 | 17 | 56 | 13 | 66.4 | 93 | 74.6 | 180 | 145 | 272 |
|  | 10 | 0 | 4 | 40 | 17 | 62.6 | 76 | 44.6 | 240 | 205 | 272 |
|  | 5 | 2.5 | 8 | 60 | 21 | 67.6 | 0 | 40.6 | 380 | 185 | 26 |
|  | 2.5 | 4.5 | 6 | 40 | 15 | 105.6 | 0 | 70.6 | 270 | 125 | 10 |
|  | 1.25 | 0 | 5 | ND | 27 | 55.6 | 0 | 33.6 | 240 | 38 | 47 |
| None |  | 2.5 | 3 | ND | ND | 66.0 | 39 | 40.6 | 460 | 80 | 135 |
| Freeze & Thaw 5× |  | 2.5 | 0 | 8 | 27 | 4.4 | 0 | 3.4 | 0 | 25 | 18 |

TABLE 5

De Novo IgE Synthesis (picograms/ml)*

| Mitogen (µg/ml) | | $1^a$ | $2^{a,b}$ | $3^b$ | $4^b$ | $5^b$ | $6^b$ | $7^{a,b}$ | $8^a$ | 9 | $10^b$ |
|---|---|---|---|---|---|---|---|---|---|---|---|
| PWM | 5 | 1,750 | 2,500 | 3,750 | 250 | 2,750 | 2,500 | 1,600 | 2,000 | <100 | 50 |
|  | 2.5 | 1,750 | 2,500 | 2,750 | 250 | 2,500 | 3,500 | 2,500 | 1,950 | <100 | ND |
| CAE | 20 | <100 | 12,250 | 8,250 | 9000 | 4,000 | 20,500 | 1,300 | 1,700 | 200 | 300 |
|  | 10 | <100 | 10,000 | 7,500 | 5000 | 2,250 | 13,000 | 450 | 1,100 | <100 | 100 |
|  | 5 | <100 | 3,750 | 2,250 | 7500 | 2,250 | 65,000 | 300 | 900 | 200 | <50 |
|  | 2.5 | <100 | 3,250 | 2,500 | 8000 | 2,250 | 3,000 | 50 | 900 | 100 | <50 |
|  | 1.25 | <100 | 6,750 | 3,500 | 2000 | 3,750 | 4,250 | <50 | 700 | <100 | <50 |
| None |  | <100 | 750 | 4,000 | 250 | 2,500 | 11,500 | 100 | 1,100 | 200 | <50 |
| 5× Freeze and thaw$^c$ |  | 100 | <100 | 2,250 | 750 | 150 | 100 | 1,200 | 100 | 650 | 300 |

$^a$PWM stimulates de novo IgE synthesis from PBL of 4 donors.
$^b$CAE stimulates de novo IgE synthesis from PBL of 7 donors.
$^c$Values of 5× freeze and thaw cells cultured for 10 days.
*Background IgE release were subtracted from each value.
ND Not determined The induction of de novo human IgG subclass synthesis—IgG$_1$ and IgG$_2$—by *Cytophaga allerginae* lipopolysaccharide endotoxin in human PBL was determined by the method of Scott and Nahm, *J. of Immunol* 135: 2454–2460(1984). The data in Table 6, below, show that the CAE is better at stimulating IgG production when compared to an *E. coli* endotoxin (Gibco). Moreover, the CAE was twice as active at high concentrations.

TABLE 6

Comparison of *E. coli* LPS with CAE

| LPS | | IgM None | E. coli | CAE | IgG None | E. coli | CAE | IgG1 None | E. coli | Cae | IgG2 None | E. coli | CAE |
|---|---|---|---|---|---|---|---|---|---|---|---|---|---|
| Donor | A | <1.5* | 1.1 | 2 | 2 | 1.1 | 2.4 | — | 0.42 | 0.69 | — | 0.23 | 0.42 |
|  | B | 0.7 | 2.2 | 4.6 | 2 | 2.8 | 4 | — | 1.4 | 2 | — | 1.1 | 1.9 |
|  | C | 0.2 | <1 | 1.1 | 0.25 | 0.8 | 1.5 | — | 0.9 | 1.35 | — | <0.28 | <0.28 |

*Units are µg/ml
**Gibco *E. coli* LPS was used at 1/100 dilution and CAE was used at 50 µg/ml.

Various other examples will be apparent to the person skilled in the art after reading the disclosure hereof without departing from the spirit and scope of the invention, and it is intended that all such examples be included in the scope of the appended claims. Thus, it will be appreciated, for example, that mutants and variants of the *Cytophaga allerginae,* ATCC 35,408, can be used as sources of the endotoxin to provide similar immunostimulation results.

What is claimed is:

1. The method of stimulating the immune system of a warm-blooded animal with a bacterial endotoxin of reduced toxicity to produce an increased level of antibodies selected from the group consisting of IgG, IgA and IgE which comprises administering to said warm-blooded animal an effective amount of *Cytophaga allerginae* lipopolysaccharide endotoxin with a pharmaceutically acceptable carrier, said reduced toxicity being determined by comparison with the toxicity produced by a *Salmonella typhosa* endotoxin control and said increased level of antibodies being determined by comparison with the antibody level produced by the stimulating effect of an *E. coli* endotoxin or pokeweed mitogen control on peripheral blood lymphocytes.

2. The method of claim 1 in which the IgG antibodies are $IgG_1$ and $IgG_2$.

* * * * *